United States Patent [19]

Stahly

[11] Patent Number: 4,952,718
[45] Date of Patent: Aug. 28, 1990

[54] REDUCTION OF CYANOHYDRINS

[75] Inventor: Barbara C. Stahly, Baton Rouge, La.

[73] Assignee: Ethyl Corporation, Richmond, Va.

[21] Appl. No.: 271,225

[22] Filed: Nov. 14, 1988

[51] Int. Cl.$^5$ ............................................. C07C 253/30
[52] U.S. Cl. ................................................... 558/388
[58] Field of Search ........................................ 558/388

[56] References Cited

U.S. PATENT DOCUMENTS 4,186,270  1/1980  Dowd et al. ................. 562/492 XR

FOREIGN PATENT DOCUMENTS 219752   8/1982  Czechoslovakia .
52-111536 9/1977  Japan .
62-126159 6/1987  Japan .

OTHER PUBLICATIONS

Fieser, et al., "Reagents for Organic Synthesis", vol. 7, (1979), p. 290.

Primary Examiner—Joseph Paul Brust
Attorney, Agent, or Firm—Patricia J. Hogan

[57] ABSTRACT

Arylacetonitriles corresponding to the formula Ar-CH(R)CN are prepared by reducing a cyanohydrin corresponding to the formula Ar-C(R)(OH)CN with phosphorus pentasulfide in an inert solvent; Ar in the formulas representing aryl and R being hydrogen or alkyl. The products are primarily useful as pharmaceutical and agricultural intermediates.

18 Claims, No Drawings

REDUCTION OF CYANOHYDRINS

FIELD OF INVENTION

This invention relates to arylacetonitriles and more particularly to a process for preparing them by the reduction of cyanohydrins.

BACKGROUND

As disclosed in Japanese Kokai No. 62-126159 (Yamauchi et al.), it is known that arylacetonitriles are useful as pharmaceutical and agricultural intermediates. Such nitriles may be prepared by known process like those taught by Yamauchi et al., Tokutake (Japanese Kokai 52-111536), Palecek et al. (Czechoslovakian Certificate of Authorship 219,752), and Dowd et al. (U.S. Pat. No. 4,186,270). However, there is a need for a more convenient process.

SUMMARY OF INVENTION

It has now been found that arylacetonitriles corresponding to the formula Ar—CH(R)CN can be prepared by reducing a cyanohydrin corresponding to the formula Ar—C(R)(OH)CN with phosphorus pentasulfide in an inert solvent; Ar in the formulas representing aryl and R being hydrogen or alkyl.

DETAILED DESCRIPTION

Cyanohydrins which may be used in the practice of the invention are compounds corresponding to the formula Ar—C(R)(OH)—CN in which Ar is aryl and R is hydrogen or alkyl.

The aryl group may be e.g., a phenyl, naphthyl, anthracyl, phenanthryl, or biphenylyl group, frequently such a group which bears one or more substituents, such as those taught by Yamauchi et al., the teachings of which are incorporated herein in toto by reference. Because of the great interest in pharmaceutical and agricultural chemicals which may be prepared from them, the preferred cyanohydrins are compounds in which Ar is a substituted or unsubstituted phenyl or naphthyl group, such as phenyl, 3-phenoxyphenyl, a 4-alkylphenyl group wherein the alkyl substituent is an alkyl group containing 1–5 carbons (e.g., methyl, ethyl, propyl, butyl, isobutyl, and pentyl groups), naphthyl, or a 6-alkoxynaphthyl group wherein the alkoxy substituent is an alkoxy group containing 1–5 carbons (e.g., methoxy, ethoxy, propoxy, butoxy, and pentoxy groups), etc.

When R of the cyanohydrin formula is alkyl, it may be a longer-chain alkyl group of up to 20 carbons or more, e.g., a hexyl, octyl, decyl, dodecyl, pentadecyl, or eicosyl group. However, it is preferably an alkyl group of 1–5 carbons, e.g., methyl, ethyl, propyl, isopropyl, butyl, isobutyl, or pentyl.

Exemplary of particularly preferable cyanohydrins are 1-cyano-1-hydroxy-1-(3-phenoxyphenyl)ethane, $\alpha$-cyano-$\alpha$-hydroxy-3-phenoxytoluene, 1-cyano-1-hydroxy-1-(4-alkylphenyl)ethanes such as 1-cyano-1-hydroxy-1-(4-isobutylphenyl)ethane, $\alpha$-cyano-$\alpha$-hydroxy-4-alkyltoluenes such as $\alpha$-cyano-$\alpha$-hydroxy-4-isobutyltoluene, 1-cyano-1-hydroxy-1-(6-methoxy-2-naphthyl)ethane, $\alpha$-cyano-$\alpha$-hydroxy-2-methyl-6-methoxynaphthalene, and their analogs and homologs.

When the cyanohydrins are not commercially available, they may be prepared by the cyanation of the appropriate aldehydes or ketones, as taught, e.g., in March, *Advanced Organic Chemistry*, Second Edition, McGraw-Hill, New York, 1977, pp. 873–874, the teachings of which are incorporated herein by reference.

The phosphorus pentasulfide with which the cyanohydrin is reduced is the material which, although commonly known as phosphorus pentasulfide, is more accurately designated as tetraphosphorus decasulfide and is commercially available as a mixture of tetraphosphorus decasulfide and tetraphosphorus nonasulfide. The commercial material is satisfactory. The amount employed is generally about 0.2–1.1 mols, preferably about: 0.5 mol, per mol of the cyanohydrin. Larger amounts may be used without a deleterious effect on the reduction, but there does not appear to be any advantage obtained by using such a substantial excess of the material.

The inert solvent employed in the reaction may be any inert solvent having a boiling point such as to make it suitable for use at the desired reaction temperature, e.g., acetonitrile, tetrahydrofuran, diglyme, diethyl ether, etc. However, when the reaction is to be conducted at reflux temperatures to speed the reaction, it is preferably an inert aliphatic, cycloaliphatic, or aromatic hydrocarbon having a boiling point of at least about 50° C., most commonly about 50°–150° C., although hydrocarbons having higher or lower boiling points may be used if desired.

Examples of hydrocarbons that can be utilized as the solvent are hexane, heptane, octane, nonane, decane, cyclopentane, cyclohexane, cycloheptane, benzene, toluene, xylene, etc., as well as the less easily available liquid hydrocarbons. Aromatic hydrocarbons such as toluene are generally preferred.

The reduction is effected by admixing the aforementioned ingredients of the reaction mixture and stirring the reaction mixture until at least a portion of the cyanohydrin has been converted to the corresponding arylacetonitrile. As indicated above, the reaction proceeds more rapidly at elevated temperatures, such as reflux temperatures. However, the formation of by-products appears to be minimized by the use of lower temperatures, so it is frequently preferred to conduct the reaction at room temperature.

After completion of the reaction, the reaction product may be acidified by known techniques, such as those taught by Yamauchi et al., Tokutake, Palecek et al., Dowd et al., and Nicholson et al. (U.S. Pat. Nos. 3,228,831 and 3,385,886), the teachings of all of which are incorporated herein in toto by reference, to prepare acids which can be used as pharmaceutical or agricultural chemicals.

The reaction product which is subjected to acidification may be the crude product of the reduction reaction or a product which has been pretreated. Examples of pretreatments which may be performed are:

(1) complete isolation of the arylacetonitrile, (2) alkylation of an Ar—CH$_2$CN reaction product, e.g., with a suitable alkyl halide such as a methyl or ethyl chloride or bromide or a dialkyl sulfate such as dimethyl or diethyl sulfate, to extend the alkyl chain, and (3) hydrogenation of the arylacetonitrile/arylacrylonitrile (i.e., Ar—CH(R)CN/Ar—C(CN)=R) mixture that is formed when R is alkyl in order to convert the unsaturated by-product to the arylacetonitrile.

The following examples are given to illustrate the invention and are not intended as a limitation thereof.

EXAMPLE I

A crude solution of 410 mg (2.0 mmol) of 1-cyano-1-hydroxy-1-(4-isobutylphenyl)ethane (IBACH) in 5 mL of toluene was treated under nitrogen with 450 mg (1.0 mmol) of a finely-ground commercial phosphorus pentasulfide which is a mixture of tetraphosphorus decasulfide and tetraphosphorus nonasulfide. The reaction mixture was stirred well and heated in an 85° C. bath for one hour. GC analysis of the crude reaction product indicated that the reaction resulted in the formation of 1-cyano-1-(4-isobutylphenyl)ethane (PN) and 2-(4-isobutylphenyl)acrylonitrile (UN) in a ratio of 2/1.

EXAMPLE II

A crude solution of 2.0 g (10 mmol) of IBACH in 25 mL of toluene was treated with 2.2 g (5.0 mmol) of the finely-ground commercial phosphorus pentasulfide of Example I and heated in an 85° C. bath for 80 minutes, after which GC analysis showed that PN and UN were formed in a ratio of 3.4/1. The reaction mixture was allowed to cool to room temperature and was then filtered through diatomaceous earth and concentrated in vacuo to an oil. After treatment with 3.5 mL of absolute ethanol and 12.8 g of 50% aqueous sodium hydroxide solution, the oil was heated at reflux for 70 minutes and then acidified with concentrated hydrochloric acid, diluted with water, and extracted with dichloromethane. GC analysis showed that the reaction resulted in the formation of ibuprofen and by-products, with minor amounts of unreacted PN and UN remaining.

EXAMPLE III

A solution of 580 mg of 77% 1-cyano-1-hydroxy-1-(3-phenoxyphenyl)ethane (2.0 mmol) and 5 mL of toluene was treated with 440 mg (1.0 mmol) of the phosphorus pentasulfide of Example I, stirred well with a magnetic stirrer, and heated at 85° C. for 40 minutes. GC analysis showed a single major peak which was identified as m-phenoxyphenylacetonitrile.

EXAMPLE IV

A solution of 600 mg of 68% IBACH (2.0 mmol) in 5 mL of toluene was treated with 440 mg (1.0 mmol) of the phosphorus pentasulfide of Example I and stirred well with a magnetic stirrer for two weeks at room temperature. GC analysis showed that PN and UN were formed in a ratio of 11/1.

It is obvious that many variations may be made in the processes set forth above without departing from the spirit and scope of this invention.

What is claimed is:

1. A process for preparing a arylacetonitrile of the formula ArCH(R)CN wherein Ar is phenyl, 3-phenoxyphenol, 4-alkylphenyl where the alkyl group has 1 to 5 carbon atoms, naphthyl or 6-alkoxynaphthyl where the alkoxy group has 1 to 5 carbon atoms and R is hydrogen or an alkyl group having 1 to 20 carbon atoms which comprises reducing a cyanohydrin of the formula ArC(R)(OH)CN where Ar and R are as previously defined with phosphorus pentasulfide, the amount of said phosphorus pentasulfide being about 0.2 to 1.1 mole per mole of said cyanohydrin in an inert solvent having a boiling point of 50° to 150° C.

2. The process of claim 1 wherein Ar is a 6-alkoxy-2-naphthyl group in which the alkoxy substituent contains 1–5 carbons.

3. The process of claim 2 wherein the cyanohydrin is 1-cyano-1-hydroxy-1-(6-methoxy-2-naphthyl)ethane.

4. The process of claim 2 wherein the cyanohydrin is α-cyano-α-hydroxy-2-methyl-6-methoxynaphthalene.

5. The process of claim 1 wherein the phosphorus pentasulfide is a mixture of tetraphosphorus decalsulfide and tetraphosphorus nonasulfide.

6. The process of claim 1 wherein the amount of phosphorus pentasulfide employed is about 0.5 mol per mol of cyanohydrin.

7. The process of claim 1 wherein the inert solvent is an inert hydrocarbon.

8. The process of claim 7 wherein the solvent is toluene.

9. The process of claim 1 wherein Ar is phenyl or 4-alkylphenyl where the alkyl group has 1 to 5 carbon atoms.

10. The process of claim 9 wherein the cyanohydrin is 1-cyano-1-hydroxy-1-(3-phenoxyphenyl)ethane.

11. The process of claim 9 wherein the cyanohydrin is α-cyano-α-hydroxy-3-phenoxytoluene.

12. The process of claim 9 wherein Ar is a 4-alkylphenyl group in which the alkyl substituent contains 1–5 carbons.

13. The process of claim 12 wherein the cyanohydrin is a 1-cyano-1-hydroxy-1-(4-alkylphenyl)ethane.

14. The process of claim 13 wherein the cyanohydrin is 1-cyano-1-hydroxy-1-(4-isobutylphenyl)ethane.

15. The process of claim 12 wherein the cyanohydrin is an α-cyano-αhydroxy-4-alkyltoluene.

16. The process of claim 15 wherein the cyanohydrin is α-cyano-α-hydroxy-4-isobutyltoluene.

17. A process for preparing 1-cyano-1-(4-isobutylphenyl)ethane which comprises reducing 1 molar proportion of 1-cyano-1-hydroxy-1-(4-isobutylphenyl)ethane with 0.5 molar proportion of a mixture of tetraphosphorus decasulfide and tetraphosphorus nonasulfide in toluene.

18. A process for preparing an arylacetonitrile of the formula ArCH(R)CN wherein Ar is 4-alkylphenyl where the alkyl group has 1 to 5 carbon atoms and R is hydrogen or an alkyl group having 1 to 20 carbon atoms which comprises (1) forming a mixture of nitriles having the formula Ar—C(CN)=R and ArCH(R)CN by reducing a cyanohydrin of the formula ArC(R)(OH)CN where Ar and R are as previously defined with phosphorus pentalsulfide, the amount of phosphorus pentasulfide being about 0.2 to 1.1 moles per mole of said cyanohydrin in an inert solvent having a boiling point of 50° to 150° C. and (2) hydrogenating the mixture of step 1.

* * * * *